United States Patent
Feng

(10) Patent No.: US 9,358,098 B2
(45) Date of Patent: Jun. 7, 2016

(54) TISSUE INGROWTH ANCHORING SYSTEMS AND METHODS AND RELATED PRODUCTS

(75) Inventor: Brian Pak-Yun Feng, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 841 days.

(21) Appl. No.: 12/706,213

(22) Filed: Feb. 16, 2010

(65) Prior Publication Data

US 2011/0202075 A1 Aug. 18, 2011

(51) Int. Cl.
- *A61F 2/848* (2013.01)
- *A61F 2/07* (2013.01)
- *A61F 2/06* (2013.01)
- *A61F 2/24* (2006.01)
- *A61F 2/89* (2013.01)

(52) U.S. Cl.
CPC . *A61F 2/07* (2013.01); *A61F 2/064* (2013.01); *A61F 2/2475* (2013.01); *A61F 2/848* (2013.01); *A61F 2/89* (2013.01); *A61F 2002/075* (2013.01); *A61F 2210/0076* (2013.01); *A61F 2220/0008* (2013.01); *A61F 2250/0024* (2013.01); *A61F 2250/0031* (2013.01); *A61F 2250/0051* (2013.01); *A61F 2250/0069* (2013.01)

(58) Field of Classification Search
CPC .................. A61F 2002/848; A61F 2250/0024; A61F 2250/0031; A61F 2250/0051; A61F 2220/0008
USPC ............ 623/1.47, 1.24, 1.26, 2.12–2.19, 1.44
See application file for complete search history.

(56) References Cited

U.S. PATENT DOCUMENTS

| | | | | |
|---|---|---|---|---|
| 3,503,079 | A * | 3/1970 | Smith | 623/2.34 |
| 5,670,161 | A * | 9/1997 | Healy et al. | 623/1.42 |
| 5,769,884 | A * | 6/1998 | Solovay | 623/1.13 |
| 5,824,037 | A * | 10/1998 | Fogarty | A61F 2/07 623/1.13 |
| 5,895,420 | A * | 4/1999 | Mirsch et al. | 623/2.38 |
| 6,391,052 | B2 * | 5/2002 | Buirge et al. | 623/1.47 |
| 6,540,780 | B1 * | 4/2003 | Zilla | A61F 2/06 623/1.39 |
| 6,638,520 | B1 * | 10/2003 | Sanders | 424/426 |
| 6,719,783 | B2 | 4/2004 | Lentz | |
| 6,951,573 | B1 * | 10/2005 | Dilling | 623/2.2 |
| 6,958,076 | B2 * | 10/2005 | Acosta et al. | 623/1.24 |
| 7,244,444 | B2 * | 7/2007 | Bates | 424/423 |
| 7,371,258 | B2 * | 5/2008 | Woo et al. | 623/2.22 |
| 8,303,650 | B2 * | 11/2012 | Shokoohi | 623/1.42 |
| 8,435,285 | B2 * | 5/2013 | Shank | A61F 2/07 623/1.38 |
| 2002/0052649 | A1 * | 5/2002 | Greenhalgh | 623/1.35 |
| 2003/0055494 | A1 * | 3/2003 | Bezuidenhout | A61F 2/04 623/1.39 |
| 2005/0065594 | A1 * | 3/2005 | DiMatteo et al. | 623/1.24 |

(Continued)

*Primary Examiner* — Thomas J Sweet
*Assistant Examiner* — Cheryl Miller
(74) *Attorney, Agent, or Firm* — Woodard, Emhardt, Moriarty, McNett & Henry LLP

(57) ABSTRACT

Described, in certain aspects, are medical devices that can be used to anchor graft materials to bodily structures. These devices comprise an implantable graft structure and tissue ingrowth material. This implantable graft structure is comprised of a body of persistent material having a first face and one or more openings defined therein, wherein the persistent material body first face is configured for opposing a bodily structure wall upon implantation. This tissue ingrowth material is positioned at the one or more persistent material body openings, and is configured for receiving tissue ingrowth from the bodily structure wall effective to anchor the graft structure to the bodily structure wall. The invention also provides methods utilizing these and other inventive medical devices, for example, to anchor graft materials to vascular vessel walls and/or other bodily structures.

33 Claims, 3 Drawing Sheets

(56) References Cited

U.S. PATENT DOCUMENTS

| | | | |
|---|---|---|---|
| 2005/0137677 A1* | 6/2005 | Rush | A61F 2/06 623/1.13 |
| 2005/0288797 A1* | 12/2005 | Howland | A61F 2/0063 623/23.74 |
| 2006/0058889 A1* | 3/2006 | Case | A61F 2/2412 623/23.68 |
| 2006/0292206 A1* | 12/2006 | Kim et al. | 424/443 |
| 2008/0077222 A1* | 3/2008 | Johnson | A61L 31/005 623/1.2 |
| 2008/0091261 A1* | 4/2008 | Long et al. | 623/1.24 |
| 2008/0119943 A1* | 5/2008 | Armstrong | A61F 2/89 623/23.7 |
| 2008/0167708 A1* | 7/2008 | Molland | A61F 2/90 623/1.17 |
| 2008/0208325 A1* | 8/2008 | Helmus | A61F 2/06 623/1.44 |
| 2009/0248144 A1* | 10/2009 | Bahler et al. | 623/1.35 |
| 2009/0276039 A1* | 11/2009 | Meretei | 623/2.14 |
| 2010/0114307 A1* | 5/2010 | Agnew et al. | 623/2.12 |
| 2010/0204775 A1* | 8/2010 | Edwin | 623/1.13 |
| 2011/0022153 A1* | 1/2011 | Schreck et al. | 623/1.13 |

* cited by examiner

TISSUE INGROWTH ANCHORING SYSTEMS AND METHODS AND RELATED PRODUCTS

BACKGROUND

The present invention relates generally to medical devices and in particular aspects to systems and methods useful for anchoring graft materials to bodily structures.

As further background, implant materials that are receptive to tissue ingrowth have found wide use in the medical arts, particularly in applications involving tissue replacement, augmentation, and/or repair. These materials may be naturally-derived or non-naturally-derived, and when they are implanted within a patient, cells and other bodily substances from the patient can infiltrate the material, leading to, for example, new tissue growth on, around, and/or within the implanted material. In some instances, collagen-containing materials have been adapted for use as implantable tissue ingrowth materials. Suitable collagenous materials can be provided by collagenous extracellular matrix (ECM) materials. Such ECM materials can be provided, for example, by materials isolated from a suitable tissue source from a warm-blooded vertebrate, e.g., from the submucosal tissue of a mammal. Such isolated submucosal tissue, for example, small intestinal submucosa (SIS), can be processed so as to have bioremodelable, angiogenic properties and promote cellular invasion and ingrowth.

As well, a variety of techniques have been developed for anchoring graft materials to bodily structures. These include but are not limited to suturing, stapling, and/or applying adhesives to graft materials, and utilizing various mechanical devices such as hooks, barbs, clips, and variations and combinations thereof. Yet, there remain needs for improved and/or alternative systems and methods for anchoring graft materials and other objects to bodily structures. There also remain needs for implantable medical products (e.g., stents, prosthetic valves, etc.) that incorporate such systems. The present invention is addressed to those needs.

SUMMARY

The present invention provides, in certain aspects, unique methods and systems for anchoring graft materials to bodily structure walls. Some inventive methods and systems involve anchoring a first graft component to a bodily structure wall, wherein the anchoring—at least in part—is provided by new tissue that grows on, around, and/or within a second graft component that is associated with the first graft component (e.g., positioned in and/or around an opening in the first graft component). Illustratively, in one inventive method, a graft structure is provided that includes a body of persistent material having a first face and one or more openings defined therein. Additionally, tissue ingrowth material is provided that is configured for receiving tissue ingrowth. The graft structure and the tissue ingrowth material are implanted at the bodily structure wall, wherein the persistent material body first face opposes the bodily structure wall, and the tissue ingrowth material is positioned at the one or more persistent material body openings to receive tissue ingrowth from the bodily structure wall effective to anchor the graft structure to the bodily structure wall. Graft structures of this sort can be anchored to any suitable bodily structure wall occurring on and/or within the body of a patient, and in this regard, inventive methods and systems can be adapted for a variety of uses. Although not necessary to broader aspects of the invention, in some forms, a graft structure replaces, repairs, augments, and/or otherwise suitably treats diseased, damaged or otherwise defective bodily tissue to which it is anchored. In other forms, a graft structure additionally or alternatively provides benefit to body parts other than that to which it is anchored.

In another embodiment, the invention provides a medical device comprised of an implantable graft structure and a tissue ingrowth material. The implantable graft structure includes a body of persistent material having a first face and one or more openings defined therein, wherein the persistent material body first face is configured for opposing a bodily structure wall upon implantation. The tissue ingrowth material is positioned at the one or more persistent material body openings, and is configured for receiving tissue ingrowth from the bodily structure wall effective to anchor the graft structure to the bodily structure wall. Such a persistent material body can exhibit a variety of shapes and sizes, and may be formed with one or more of a variety of biocompatible materials including some that are naturally derived and some that are non-naturally derived. Illustratively, a persistent material body can be or include a generally planar sheet-form or sheet-like construct. In some embodiments, a persistent material body is comprised of a non-sheet-form construct. As well, the tissue ingrowth material may be comprised of any suitable material, and can be positioned and configured in a variety of fashions at the one or more persistent material body openings for receiving tissue ingrowth. Although not necessary to broader aspects of the invention, in some embodiments, the persistent material body and the tissue ingrowth material are dissimilar in their propensity for receiving and/or promoting tissue ingrowth, yet are comprised of one or more of the same materials. In some preferred aspects, the persistent material body includes a synthetic polymeric material, and the tissue ingrowth material includes a remodelable, angiogenic material, for example, a remodelable extracellular matrix material such as submucosa.

Other objects, embodiments, forms, features, advantages, aspects, and benefits of the present invention shall become apparent from the detailed description and drawings included herein.

DETAILED DESCRIPTION

Figure 1A:
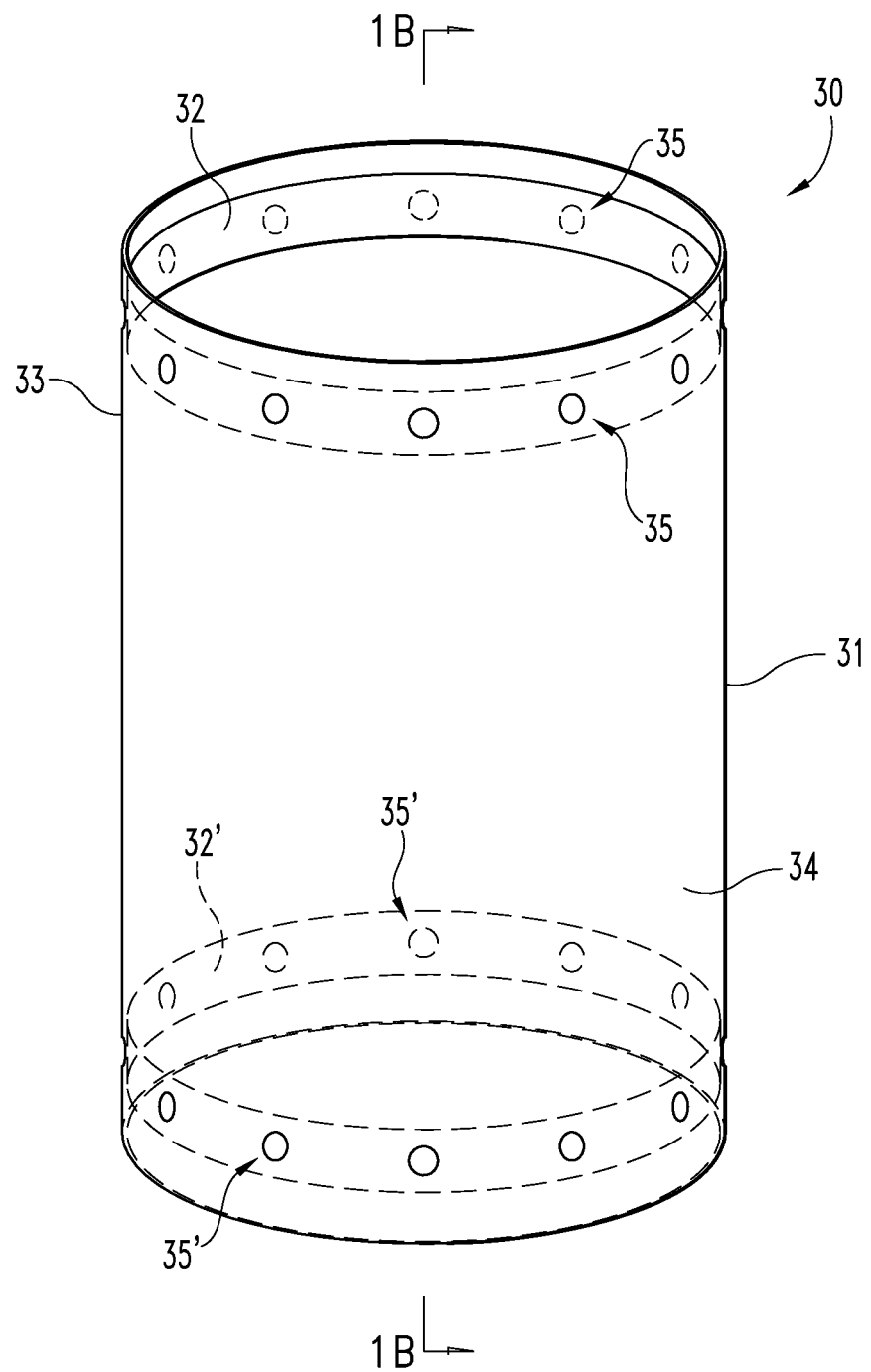
FIG. 1A is a perspective view of a medical device of the invention.

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

The present invention provides, in certain aspects, medical constructs utilizing tissue ingrowth materials. One such construct includes a body of persistent material having a first face and one or more openings defined therein, wherein the persistent material body first face is configured for opposing a bodily structure wall upon implantation. The construct also includes a tissue ingrowth material that is positioned at the one or more persistent material body openings, and is configured for receiving tissue ingrowth effective to anchor the construct to the bodily structure wall. A persistent material body of this sort may be formed with one or more of a variety of biocompatible materials. In some preferred aspects, a persistent material body comprises a synthetic polymeric material such as ePTFE or THORALON®, although the use of a synthetic material for the persistent material body is not necessary to broader aspects of the invention. The tissue ingrowth material, as well, may be formed with one or more of a variety of biocompatible materials including some that are naturally derived and some that are non-naturally derived. In some preferred aspects, the tissue ingrowth material includes a remodelable, angiogenic material, for example, a remodelable extracellular matrix material such as submucosa. The invention also provides systems and methods for anchoring graft materials to bodily structure walls, e.g., for anchoring stents, prosthetic valves, etc. to vascular vessel walls.

Persistent material bodies useful in the present invention may be formed with naturally-derived materials, non-naturally-derived materials, or both. By "persistent", it is meant that the material can persist at an implantation site (e.g., on or within the body of a patient) for a period of time after implantation. For a given persistent material body utilized in the invention, this time period can vary, for example, by selecting different materials of construction and/or by manipulating one or more physical, chemical, biological and/or other properties of a material used. In some forms, a persistent material body will be configured to persist at an implantation site for an extended period of time (e.g., for several years or for a length of time easily exceeding the expected lifespan of the implant recipient), and in this regard, will be considered essentially non-biodegradable or having a very slow rate of degradation. In other forms, a persistent material body will be configured to persist for a relatively shorter time period (e.g., for a few weeks or months) before at least partially degrading. In certain aspects of the invention, a persistent material body will be formed with a naturally derived material (e.g., a collagen-containing material derived from a mammalian tissue source) that has been treated in some manner to increase its ability to persist in the body. Illustratively, a material, which would otherwise fully degrade in the body following implantation, can be treated such that it becomes essentially non-biodegradable or its rate of degradation in the body is lowered.

Persistent material bodies useful in some aspects of the invention are formed with synthetic polymeric materials (e.g., non-bioresorbable or biostable plastics).

These materials include but are not limited to polytetrafluoroethylene (PTFE) (including expanded PTFE), polyethylene terephthalate (PET), polyurethanes, silicones, and polyesters and other polymers such as, but not limited to, polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; and rayon-triacetate. These materials may be in any suitable form, for example, yarns, fibers, and/or resins. Further, the present invention contemplates other plastic, resin, polymer, woven, and fabric surgical materials, other conventional synthetic surgical materials, such as a shape-memory plastic, and/or combinations of such materials.

Additionally, a variety of biocompatible polyurethane materials can be used to form a persistent material body useful in the present invention. One such material is THORALON® (THORATEC, Pleasanton, Calif.), described in U.S. Pat. Application Publication No. 2002/0065552 A1 and U.S. Pat. No. 4,675,361, both of which are incorporated herein by reference. The biocompatible polyurethane material sold under the tradename THORALON® is a polyurethane base polymer (referred to as BPS-215) blended with a siloxane containing surface modifying additive (referred to as SMA-300). The concentration of the surface modifying additive may be in the range of 0.5% to 5% by weight of the base polymer.

The SMA-300 component (THORATEC) is a polyurethane comprising polydimethylsiloxane as a soft segment and the reaction product of diphenylmethane diisocyanate (MDI) and 1,4-butanediol as a hard segment. A process for synthesizing SMA-300 is described, for example, in U.S. Pat. Nos. 4,861,830 and 4,675,361, which are incorporated herein by reference.

The BPS-215 component (THORATEC) is a segmented polyetherurethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED).

Various forms of THORALON® may be utilized in the present invention, and in this regard, a particular THORALON® material may be selected based on one or more characteristics of the material such as but not limited to its ability to inhibit thrombosis, tensile strength, resistance to water absorption, critical surface tension, flexibility, flex life and the like.

Persistent material bodies useful in the invention can be shaped and configured in a variety of manners. In some forms, a persistent material body comprises a single- or multi-layer sheet-form material, for example, exhibiting a rectangular, circular or other suitable shape. Such bodies may be shaped and configured according to various patches, dressings and other medical materials known in the art. Bodies of this sort can be useful, for example, in supporting and/or otherwise treating wounded, diseased or otherwise damaged tissue. In some instances, a persistent material body includes sheet-form material that has been transformed into a different shape, for example, where one or more material layers have been rolled and/or folded in some manner, e.g., into a generally cylindrical or conical shape. While not necessary to broader aspects of the invention, such constructs may have a central lumen extending fully or partially through the construct along its length. The thickness and other dimensions of a particular sheet-form body, or portion thereof, can vary to suit a particular application.

In some embodiments, a persistent material body includes a portion not in the form of a sheet. Illustratively, such a non sheet-form portion can have a three-dimensional rectilinear or curvilinear shape. Such three-dimensional rectilinear shapes can have any suitable number of sides, and may include, for example, cubes, cuboids, tetrahedrons, prisms, pyramids, wedges, and variations thereof. Suitable three-dimensional curvilinear shapes include but are not limited to spheres, spheroids, ellipsoids, cylinders, cones, and variations thereof (e.g., a segment of a sphere, or a truncated cone, etc.). These constructs can be formed in any suitable manner including but not limited to by extrusion, using a mold or form, construction around a mandrel, and/or combinations or variations thereof. In some embodiments, a three-dimensional construct is formed with a reconstituted or otherwise reassembled polymeric material. As well, any of these persistent material bodies can have one or more hollow portions therein.

Turning now to a more detailed discussion of tissue ingrowth materials, it should be noted that a wide variety of materials may be used in the present invention for tissue ingrowth anchoring purposes. Advantageously, these materials, whether naturally-derived or non-naturally-derived, will be such that when they are implanted within a patient, cells and other bodily substances from the patient can infiltrate the material, leading to, for example, new tissue growth on, around, and/or within the tissue ingrowth material. In this regard, when a medical device incorporating a persistent material body and tissue ingrowth material in accordance with the present invention is implanted at a bodily structure (e.g., alongside a bodily structure wall), the suitably positioned tissue ingrowth material will be able to effectively anchor the persistent material body to the bodily structure upon receiving sufficient tissue ingrowth from the patient.

Tissue ingrowth material, whether provided as a single piece of material or as multiple pieces (or amounts) of material, can be placed at a variety of locations in and/or around a persistent body to participate in an anchoring process. In some instances, tissue ingrowth material will be fully or partially embedded within a persistent material body. In general, the selection and configuration of a tissue ingrowth material, as well as its positioning in and/or around a persistent material body (e.g., in and/or around one or more persistent material body openings), will be such that upon sufficient tissue ingrowth on, around and/or within the tissue ingrowth material, a suitable anchoring arrangement will be provided. In some instances, such an arrangement will be effective to generally maintain the construct at a site in the body despite the application of bodily and/or other forces to the body to move it from the site. These forces, in some embodiments, will be overcome by new, grown-in tissue and/or the provided tissue ingrowth material, which contacts portions of the persistent material body adjacent to one or more openings in the persistent material body.

A tissue ingrowth material useful in the present invention can be formed with one or more of a variety of materials including some that are naturally derived and some that are non-naturally derived. In general, these materials will be biocompatible, and in advantageous embodiments of the invention, are comprised of a remodelable material. Particular advantage can be provided by tissue ingrowth materials that include a remodelable collagenous material. Such remodelable collagenous materials, whether reconstituted or non-reconstituted, can be provided, for example, by collagenous materials isolated from a warm-blooded vertebrate, and especially a mammal. Such isolated collagenous material can be processed so as to have remodelable, angiogenic properties and promote cellular invasion and ingrowth. Remodelable materials may be used in this context to promote cellular growth within and/or around a space in which the tissue ingrowth material is implanted, e.g., in and around a persistent material body opening.

Suitable remodelable materials can be provided by collagenous extracellular matrix (ECM) materials possessing biotropic properties. For example, suitable collagenous materials include ECM materials such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. Submucosa useful in the present invention can be obtained by harvesting such tissue sources and delaminating the submucosa from smooth muscle layers, mucosal layers, and/or other layers occurring in the tissue source. For additional information as to submucosa useful in the present invention, and its isolation and treatment, reference can be made, for example, to U.S. Pat. Nos. 4,902,508, 5,554,389, 5,993,844, 6,206,931, and 6,099,567.

Submucosa or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 $\mu$g/mg, more preferably less than about 2 $\mu$g/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of any ECM tissue used in the present invention.

A typical layer thickness for an as-isolated submucosa or other ECM tissue layer used in the invention ranges from about 50 to about 250 microns when fully hydrated, more typically from about 50 to about 200 microns when fully hydrated, although isolated layers having other thicknesses may also be obtained and used. These layer thicknesses may vary with the type and age of the animal used as the tissue source. As well, these layer thicknesses may vary with the source of the tissue obtained from the animal source.

Suitable bioactive agents may include one or more bioactive agents native to the source of the ECM tissue material. For example, a submucosa or other remodelable ECM tissue material may retain one or more growth factors such as but not limited to basic fibroblast growth factor (FGF-2), transforming growth factor beta (TGF-beta), epidermal growth factor (EGF), cartilage derived growth factor (CDGF), and/or platelet derived growth factor (PDGF). As well, submucosa or other ECM materials when used in the invention may retain other native bioactive agents such as but not limited to proteins, glycoproteins, proteoglycans, and glycosaminoglycans. For example, ECM materials may include heparin, heparin sulfate, hyaluronic acid, fibronectin, cytokines, and the like. Thus, generally speaking, a submucosa or other ECM material may retain one or more bioactive components that induce, directly or indirectly, a cellular response such as a change in cell morphology, proliferation, growth, protein or gene expression.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of such native bioactive components, non-native bioactive components such as those synthetically produced by recombinant technology or other methods (e.g., genetic material such as DNA), may be incorporated into an ECM material. These non-native bioactive components may be naturally-derived or recombinantly produced proteins that correspond to those natively occurring in an ECM tissue, but perhaps of a different species. These non-native bioactive components may also be drug substances. Illustrative drug substances that may be added to materials include, for example, anti-clotting agents, e.g. heparin, antibiotics, anti-inflammatory agents, thrombus-promoting substances such as blood clotting factors, e.g., thrombin, fibrinogen, and the like, and anti-proliferative agents, e.g. taxol derivatives such as paclitaxel. Such non-native bioactive components can be incorporated into and/or onto ECM material in any suitable manner, for example, by surface treatment (e.g., spraying) and/or impregnation (e.g., soaking), just to name a few. Also, these substances may be applied to the ECM material in a premanufacturing step, immediately prior to the procedure (e.g., by soaking the material in a solution containing a suitable antibiotic such as cefazolin), or during or after engraftment of the material in the patient.

Medical devices of the invention, in certain aspects, include xenograft material (i.e., cross-species material, such as tissue material from a non-human donor to a human recipient), allograft material (i.e., interspecies material, with tissue material from a donor of the same species as the recipient), and/or autograft material (i.e., where the donor and the recipient are the same individual). Further, any exogenous bioactive substances incorporated into an ECM material, when used in the invention, may be from the same species of animal from which the ECM material was derived (e.g. autologous or allogenic relative to the ECM material) or may be from a different species from the ECM material source (xenogenic relative to the ECM material). In certain embodiments, ECM material will be xenogenic relative to the patient receiving the graft, and any added exogenous material(s) will be from the same species (e.g. autologous or allogenic) as the patient receiving the graft. Illustratively, human patients may be treated with xenogenic ECM materials (e.g. porcine-, bovine- or ovine-derived) that have been modified with exogenous human material(s) as described herein, those exogenous materials being naturally derived and/or recombinantly produced.

ECM materials, when used in the invention, may be free of additional, non-native crosslinking, or may contain additional crosslinking. Such additional crosslinking may be achieved by photo-crosslinking techniques, by chemical crosslinkers, or by protein crosslinking induced by dehydration or other means. However, because certain crosslinking techniques, certain crosslinking agents, and/or certain degrees of crosslinking can destroy the remodelable properties of a remodelable material, where preservation of remodelable properties is desired, any crosslinking of the remodelable ECM material can be performed to an extent or in a fashion that allows the material to retain at least a portion of its remodelable properties. Chemical crosslinkers that may be used include for example aldehydes such as glutaraldehydes, diimides such as carbodiimides, e.g., 1-ethyl-3-(3-dimethylaminopropyl)carbodiimide hydrochloride, ribose or other sugars, acyl-azide, sulfo-N-hydroxysuccinamide, or polyepoxide compounds, including for example polyglycidyl ethers such as ethyleneglycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule.

Turning now to a discussion of drying techniques that can be useful in certain embodiments of the invention, drying by evaporation, or air drying, generally comprises drying a partially or completely hydrated remodelable material by allowing the hydrant to evaporate from the material. Evaporative cooling can be enhanced in a number of ways, such as by placing the material in a vacuum, by blowing air over the material, by increasing the temperature of the material, by applying a blotting material during evaporation, or by any other suitable means or any suitable combination thereof. The amount of void space or open matrix structure within an ECM material that has been dried by evaporation is typically more diminished than, for example, an ECM material dried by lyophilization as described below.

A suitable lyophilization process can include providing an ECM material that contains a sufficient amount of hydrant such that the voids in the material matrix are filled with the hydrant. The hydrant can comprise any suitable hydrant known in the art, such as purified water or sterile saline, or any suitable combination thereof. Illustratively, the hydrated material can be placed in a freezer until the material and hydrant are substantially in a frozen or solid state. Thereafter, the frozen material and hydrant can be placed in a vacuum chamber and a vacuum initiated. Once at a sufficient vacuum, as is known in the art, the frozen hydrant will sublime from the material, thereby resulting in a dry remodelable material.

In alternative embodiments, a hydrated ECM material can be lyophilized without a pre-freezing step. In these embodiments, a strong vacuum can be applied to the hydrated material to result in rapid evaporative cooling which freezes the hydrant within the ECM material. Thereafter, the frozen hydrant can sublime from the material thereby drying the ECM material. Desirably, an ECM material that is dried via lyophilization maintains a substantial amount of the void space, or open matrix structure, that is characteristic of the harvested ECM material.

Drying by vacuum pressing generally comprises compressing a fully or partially hydrated remodelable material while the material is subject to a vacuum. One suitable method of vacuum pressing comprises placing a remodelable material in a vacuum chamber having collapsible walls. As the vacuum is established, the walls collapse onto and compress the material until it is dry. Similar to evaporative drying, when a remodelable material is dried in a vacuum press, more of the material's open matrix structure is diminished or reduced than if the material was dried by lyophilization.

In certain aspects, the invention provides a medical device including a multilaminate material. Such multilaminate materials can include a plurality of ECM material layers bonded together, a plurality of non-ECM materials bonded together, or a combination of one or more ECM material layers and one or more non-ECM material layers bonded together. To form a multilaminate ECM material, for example, two or more ECM segments are stacked, or one ECM segment is folded over itself at least one time, and then the layers are fused or bonded together using a bonding technique, such as chemical cross-linking or vacuum pressing during dehydrating conditions. An adhesive, glue or other bonding agent may also be used in achieving a bond between material layers. Suitable bonding agents may include, for example, collagen gels or pastes, gelatin, or other agents including reactive monomers or polymers, for example cyanoacrylate adhesives. As well, bonding can be achieved or facilitated between ECM material layers using chemical cross-linking agents such as those described above. A combination of one or more of these with dehydration-induced bonding may also be used to bond ECM material layers to one another.

A variety of dehydration-induced bonding methods can be used to fuse together portions of an ECM material. In one preferred embodiment, multiple layers of ECM material are compressed under dehydrating conditions. In this context, the term "dehydrating conditions" is defined to include any mechanical or environmental condition which promotes or induces the removal of water from the ECM material. To promote dehydration of the compressed ECM material, at least one of the two surfaces compressing the matrix structure can be water permeable. Dehydration of the ECM material can optionally be further enhanced by applying blotting material, heating the matrix structure or blowing air, or other inert gas, across the exterior of the compressed surfaces. One particularly useful method of dehydration bonding ECM materials is lyophilization.

Another method of dehydration bonding comprises pulling a vacuum on the assembly while simultaneously pressing the assembly together. Again, this method is known as vacuum pressing. During vacuum pressing, dehydration of the ECM materials in forced contact with one another effectively bonds the materials to one another, even in the absence of other agents for achieving a bond, although such agents can be used while also taking advantage at least in part of the dehydration-induced bonding. With sufficient compression and dehydration, the ECM materials can be caused to form a generally unitary ECM structure.

It is advantageous in some aspects of the invention to perform drying and other operations under relatively mild temperature exposure conditions that minimize deleterious effects upon any ECM materials being used, for example native collagen structures and potentially bioactive substances present. Thus, drying operations conducted with no or substantially no duration of exposure to temperatures above human body temperature or slightly higher, say, no higher than about 38° C., will preferably be used in some forms of the present invention. These include, for example, vacuum pressing operations at less than about 38° C., forced air drying at less than about 38° C., or either of these processes with no active heating—at about room temperature (about 25° C.) or with cooling. Relatively low temperature conditions also, of course, include lyophilization conditions.

Whether remodelable or non-remodelable, a tissue ingrowth material useful in the present invention may be selected based on one or more physical, mechanical, biological, chemical and/or other characteristics of the material such as but not limited to its receptivity to tissue ingrowth, and in some cases, its ability to promote and/or facilitate tissue ingrowth. It should be noted that the rate and amount of tissue growth in and/or around a tissue ingrowth material can be influenced by a number of factors including but not limited to the amount of open space available in the material's matrix structure for the infusion and support of a patient's tissue-forming components, such as fibroblasts. Therefore, a more open matrix structure can provide for quicker, and potentially more, growth of patient tissue in and/or around the structure, and when remodelable materials are being used, can lead to quicker remodeling of the material by patient tissue.

In this regard, the tissue ingrowth materials used in the present invention can have a level or degree of porosity. In certain embodiments, the porosity of a segment of ECM material is lowered by drying the material under compression. In general, compressing a pliable, open matrix material, such as a pliable ECM material, increases the material's bulk density and decreases the material's porosity by decreasing the size of the voids in the open matrix. As is the case in certain aspects of the invention, when such a material is dried while being compressed, particularly under vacuum pressing conditions, the open matrix structure can become somewhat fixed in this relatively higher bulk density, lower porosity state (i.e., in a relatively more collapsed state). It should be noted that different compressing and drying methods, including different degrees of compressing and drying, can be designed through routine experimentation so as to allow for a material segment having an optimal degree of material bulk density and/or porosity for a particular anchoring application.

Referring now to FIG. 1A, shown is an illustrative medical device 30 of the present invention. Medical device 30 includes graft structure 31 and tissue ingrowth material segments 32 and 32'. Graft structure 31 is comprised of a hollow, generally cylindrical body 33 having a first face 34 and opposing rows of openings 35 and 35' occurring therein (with each row proximate one end of body 33). Although not necessary to broader aspects of the invention, the openings in each of rows 35 and 35' are of the same general size and circular shape, and are positioned generally equidistant from one another circumferentially around body 33. Body 33 is formed with a persistent material such as any of those described herein (e.g., PTFE, THORALON®, crosslinked collagen, etc.).

Persistent material body first face 34 is configured for opposing a bodily structure wall (e.g., an inner surface of a venous, arterial or other bodily vessel wall) when device 30 is suitably implanted within a patient. Tissue ingrowth material segments 32 and 32' are positioned within body 33, and provide tissue ingrowth material at the openings of rows 35 and 35', respectively, for receiving tissue ingrowth from the bodily structure wall effective to anchor graft structure 31 to the bodily structure wall. Tissue ingrowth material segments 32 and 32' can be attached to persistent material body 33 with an adhesive, sutures and/or other suitable attachment means. However, as described more thoroughly below, tissue ingrowth material need not be attached to a persistent material body to be effectively used in the invention. In some embodiments, tissue ingrowth material that is not attached to a persistent material body is suitably held or otherwise positioned at one or more persistent material body openings to receive tissue ingrowth from a bodily structure wall effective to anchor the persistent material body to the bodily structure wall.

While the device depicted in FIG. 1A is certainly useful, it represents but one embodiment of the present invention. Other devices having different numbers of openings, differently sized and shaped openings, differently positioned openings and/or the like, are contemplated in the present invention. Also, persistent material bodies and tissue ingrowth segments useful in the invention may be shaped and configured differently than what is depicted in FIG. 1A. For example, some inventive devices may have an individual piece or amount of tissue ingrowth material positioned at each of the one or more openings occurring in the persistent material body. As well, a tissue ingrowth material may cover all or part of a persistent material body surface such as the inner surface of body 33.

The bodily structures to which products of the invention can be anchored are many and include any suitable bodily structure occurring on and/or within the body of a patient. Illustratively, inventive devices can be configured for placement at bodily structures that are considered cutaneous, subcutaneous and/or intracutaneous. In some aspects, inventive products are adapted for application to subcutaneous tissue structures that may or may not include wounded tissue, e.g., to support a surgically repaired hernia. In other aspects, inventive products are adapted for application to cutaneous tissue structures such as to ulcers or burns to the skins.

In this regard, it will be understood that devices and systems of the present invention have broad application, particularly in areas of medicine that involve anchoring graft materials to bodily structures to treat those bodily structures and/or otherwise provide benefit to the implant recipient as a result of receiving the implant. Illustratively, medical devices of the invention can be configured as tissue support devices, devices suitable for bulking tissue, hemostatic devices, occlusive devices (e.g., for providing occlusion in a passageway or other open space within the body of a patient), as flow modification devices (e.g., valves such as vascular valves). In some forms, a patch or patch-like product is used as a tissue support device in a hernia repair procedure. Devices of the invention can also be adapted to carry one or more drugs or other therapeutic substances for release in the body following implantation. The invention also provides, in certain aspects, methods that utilize such devices, for example, to replace, augment, repair, and/or otherwise suitably treat diseased or otherwise damaged or defective patient tissue.

Figure 1B:
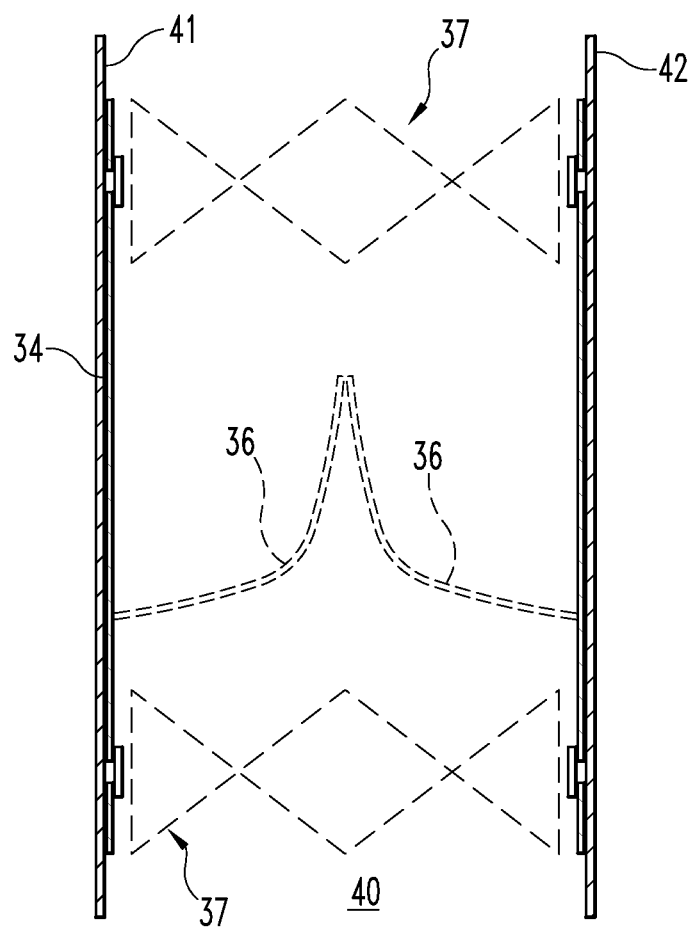
FIG. 1B provides a partial, cross-sectional view of the medical device of FIG. 1A (along the view line 1B-1B shown in FIG. 1A) implanted within a bodily passage.

In some aspects, inventive devices such as device 30 are configured for implantation within a bodily passage or other opening, for example, within a vascular vessel such as a vein or artery. Referring now to FIG. 1B, shown is medical device 30 implanted within bodily passage 40 such that persistent material body first face 34 opposes an interior surface 41 of bodily structure wall 42. In this implantation arrangement, cells and other bodily substances from the patient, including but not limited to those associated with nearby portions of vessel wall 42, can infiltrate the tissue ingrowth material, leading to, for example, new tissue growth on, around, and/or within the tissue ingrowth material to provide tissue ingrowth anchors. Once sufficient tissue growth into the tissue ingrowth material segments 32 and 32' has occurred, normal bodily forces acting to pull the persistent material body 33 away from the bodily structure at the various anchoring points will be overcome, for example, by the newly-formed tissue ingrowth anchors contacting portions of the persistent material body 33 at and around the openings of rows 35 and 35' (e.g., at locations on the inside of the persistent material body wall extending away from the edge of the openings).

Constructs according to certain aspects of the invention can be adapted to perform a variety of functions on and/or within the body of a patient. For example, in certain embodiments, inventive devices of various shapes and sizes are configured for implantation within a bodily passage to beneficially modify, alone or in combination with one or more other objects, fluid flow within the bodily passage. In some aspects of the invention, persistent material bodies are used as exterior, interior, and/or other coverings for supporting frames including but not limited to those used to provide stents and valve structures. These applications include, for example, those utilizing self-expanding or otherwise expandable frames. In one mode of forming a valve structure, a persistent material is attached to a frame in a fashion whereby it forms one, two, or more leaflets, cusps, pockets or similar structures that resist flow in one direction relative to another. In a specific application, such devices are constructed as implantable vascular valves to treat venous insufficiencies in humans, for example, occurring in the legs. In other applications, valves for treating these or other valve deficiencies may be surgically created without the use of a frame or other supporting structure. For example, a persistent material body can be adapted to provide a monocusp valve in a vascular vessel, or, alternatively, it can be adapted to provide a multicuspid valve in a vascular vessel, wherein the multicuspid valve comprises a plurality of cusps. In this respect, such materials can be adapted to provide a bicuspid valve, a tricuspid valve, or a quadracuspid valve in a vascular vessel, wherein any of these valves may or may not be attached to or otherwise associated with one or more frame elements.

Illustratively, a device such as device 30 can be configured to provide a valvular function, e.g., by incorporating one or more valve leaflets into the device. Such a device can then be implanted within a vascular vessel to, for example, replace and/or supplement an incompetent or destroyed cardiac or venous valve in the vessel. As depicted in FIG. 1B, a plurality of leaflets 36 can be disposed within persistent material body 33 for extending into the lumen of bodily passage 40 and participating with one another in a coapting arrangement in response to fluid flow in the bodily passage. Although not necessary to broader aspects of the present invention, persistent materials utilized in such embodiments may be selected based at least in part on their anti-adhesion and/or anti-calcification characteristics.

FIG. 1B shows a potential attachment path (in phantom) for the edges of leaflets 36 extending in a direction generally both longitudinally and circumferencially around the persistent material body 33. Although the leaflets shown in FIG. 1B provide a bi-leaflet valve, it should be noted that other aspects of the present invention provide valve-containing devices having one, two, three or any suitable number of leaflets. Also, it will be understood that leaflets such as leaflets 36, when utilized in the invention, can be incorporated into a construct (e.g., attached to a persistent material body) in any suitable manner including but not limited to with mechanical or other coupling elements (e.g., sutures) and/or by bonding, welding, etc.

Once implanted at a body location, devices of the present invention need to remain at this general location for a period of time at least sufficient for tissue ingrowth anchoring to occur. Depending on a number of factors such as but not limited to the configuration of the parts of the construct, the type of tissue ingrowth material(s) selected for use, and the environment in which the construct is implanted, this period of time can vary. As well, the manner in which the device is held (or otherwise caused to remain) at a body location can vary in accordance with the present invention. Objects and materials used to hold a device in place may or may not be incorporated into the device itself. For example, in some embodiments, one or more removable objects that are separate from the device (e.g., a suture and/or a mechanical device such as an expandable balloon catheter or resilient frame) are used to hold the device in place, and then are removed after desirable anchoring has occurred. Additionally or alternatively, one or more bioabsorbable or otherwise biodegradable objects and/or substances may be used to hold the device in place at least until desirable anchoring has occurred. It should be noted that these biodegradable objects may be connected to the persistent material, the tissue ingrowth material, or both.

Illustratively, one or more expandable frame elements such as those depicted in FIG. 1B can be used to suitably hold a grafting device in place while desirable tissue ingrowth anchoring occurs. Frame elements 37 are bioabsorbable, and are adapted to hold medical device 30 in place (by exerting radial force on the inside of device 30 to hold first face 34 against bodily structure wall 42) at least until graft body 33 can remain anchored without assistance from frame elements 37. In broader aspects of the invention, suitable holding means need not necessarily hold a grafting device, or any portion thereof, in direct contact with a bodily structure for desirable tissue ingrowth anchoring to occur. In some forms, a portion of an implanted device does not initially contact an adjacent bodily structure, yet new tissue growth in, on and/or within implanted tissue ingrowth material eventually grows into an adjacent bodily structure to form a tissue ingrowth anchor.

In certain aspects, sheet or sheet-like grafts (either single- or multilayered) provide wound healing products suitable for cutaneous, intracutaneous, and/or subcutaneous wound treatment, e.g., as a hernia repair patch or a cutaneous wound (e.g., burn, ulcer, etc.) treatment product. In some forms, multilaminate sheet-form devices of the invention will be constructed so as to provide an overall device thickness of at least about 150 microns, typically ranging from about 150 to about 1000 microns, and in certain embodiments ranging from about 200 to about 1000 microns. In addition to such thicknesses, typical graft products of the invention in sheet-form will have lengths and widths ranging from about 2 cm to about 50 cm.

Alternatively, graft products of the invention may find use as precursor materials for forming a variety of other medical devices, or components thereof. Illustratively, graft materials of the invention can be processed into various shapes and configurations, for example, into a urethral sling or a prosthetic body part. In some forms, sheet-form graft materials of the invention are suitable for forming tubular grafting devices, which may be used to replace a circulation vessel, or a portion thereof, or to bypass a blocked vessel.

Figure 2:
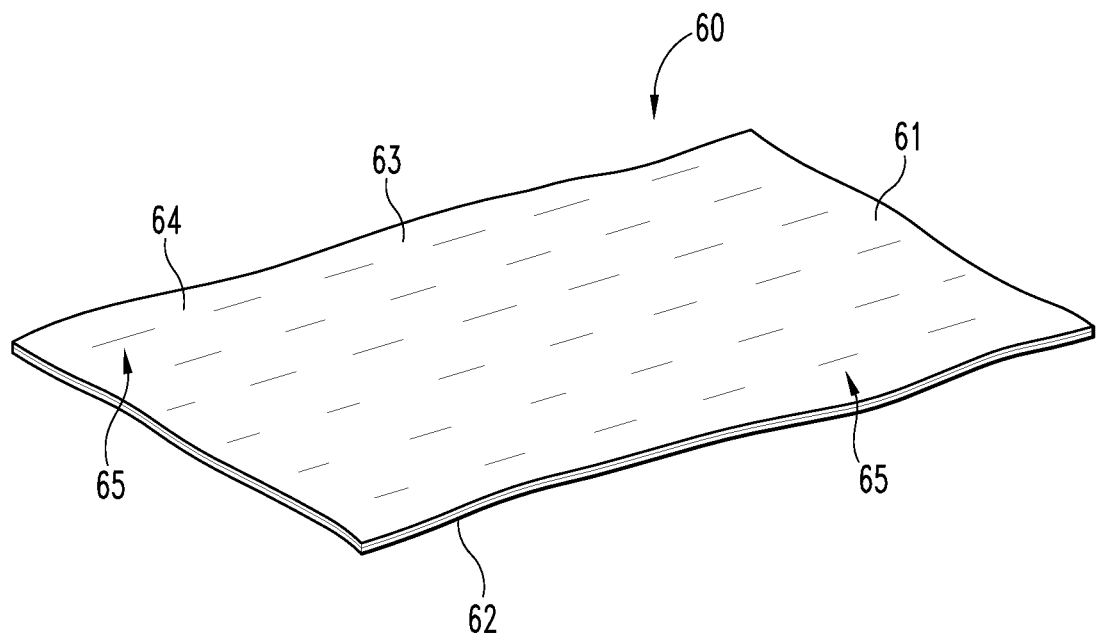
FIG. 2 is a perspective view of another medical device of the invention.

With reference now to FIG. 2, shown is another illustrative medical device 60 of the present invention. Medical device 60 is generally in the form of a sheet, and includes graft structure 61 and tissue ingrowth material 62. Graft structure 61 includes sheet-form body 63, which has a first face 64 and a plurality of openings 65 defined therein. Openings 65 are in the form of slits, which extend through body 63, and provide a meshed pattern across the sheet. In particular, the slits are arranged in a plurality of relatively parallel rows, wherein the termini of the slits in a particular row are offset relative to the termini of the slits in an adjacent row, although other suitable slit arrangements are contemplated as within the scope of the present invention. Sheet-form body 63 is formed with a persistent material, and body first face 64 is configured for opposing a bodily structure wall when device 60 is suitably implanted within a patient. Tissue ingrowth material 62 is also in the form sheet, and is attached to and generally overlaps sheet-form body 63. In this configuration, tissue ingrowth material is positioned at the persistent material body openings 65 for receiving tissue ingrowth from such a bodily structure wall effective to anchor graft structure 61 to the bodily structure wall. In an additional embodiment, device 60 includes another sheet of persistent material in an overlapping relationship with tissue ingrowth material sheet 62 so that sheet 62 is positioned between the two persistent material sheets. As well, other suitable combinations and variations of one or more sheets of tissue ingrowth material with one or more sheets of persistent material will be recognized by the skilled artisan and are encompassed by the present invention.

Illustratively, a meshed structure such as body 63 can have a plurality of slits therein to provide a mesh pattern, and the mesh pattern can be useful to provide deformability to the structure, and in some case, expandability. In this regard, in some meshed constructs, expansion or other deformation of the structure will widen the openings created by the slits of the mesh pattern, by lateral and/or vertical displacement of the edges of the slits relative to one another. Certain meshed devices of the invention will have a mesh pattern providing an expansion ratio of at least about 1.2:1 when the layer is completely hydrated, more preferably at least about 2:1, and most preferably at least about 3:1. Such highly deformable structures provide surprisingly beneficial properties to the graft product, particularly in the field of wound care.

A meshed pattern can be created using suitable meshing devices designed for processing skin autograft sections. Such devices can include a cylindrical drum cutter with a plurality of edges for providing the slit pattern of the mesh. A variety of such devices are known and can be used in the invention. For additional information as to meshers, reference may be made to U.S. Pat. Nos. 5,004,468, 6,063,094, 3,472,228, 3,358,688, and 3,640,279. These and other devices incorporating a meshing drum provide for a convenient, high-throughput method of preparing meshed material layers or graft devices of the invention. It will be understood, however, that the mesh pattern can be made by hand-cutting the material or by using appropriate cutting tools with multiple blades to cut the slits to provide the mesh pattern.

A wide variety of persistent material body openings may be employed in the present invention. In this regard, a particular persistent material body may include any suitable number of individual openings positioned randomly or non-randomly in the body, wherein each of these openings can exhibit any suitable size, shape and configuration. For example, a persistent material body opening, or any portion thereof, can be defined by a suitably shaped void (e.g., a three-dimensional rectilinear or curvilinear void) that resides in a portion of a persistent material body and communicates with a surface of the persistent material body configured to be positioned at a bodily structure for anchoring to that bodily structure. Such three-dimensional rectilinear shapes can have any suitable number of sides, and can include, for example, cubes, cuboids, tetrahedrons, prisms, pyramids, wedges, and variations thereof. Suitable three-dimensional curvilinear bodies include but are not limited to spheres, spheroids, ellipsoids, cylinders, cones, and variations thereof (e.g., a segment of a sphere, or a truncated cone, etc.).

Further in this regard, any opening in a persistent material body can extend through all or a portion of the body. Illustratively, a body such as a hollow, tubular persistent material body can have openings extending entirely through a wall of the body, e.g., from an exterior surface to an interior surface of the wall, or alternatively, only partially through a wall of the body. Also, the spacing and size of an opening in a persistent material body relative to another opening in the body, as well as the depth to which a particular opening extends into a body (if not extending entirely through the body, or a portion thereof) can vary. In some forms, at least a portion of an opening is defined by a generally cylindrical void of a suitable length and having a diameter ranging from about 0.05 mm to about 50 mm, more typically from about 2 mm to about 10 mm, and even more typically from about 3 mm to about 6 mm. These and other persistent material body openings useful in the present invention can be spaced any suitable distance from one another, and in some embodiments, are positioned in a particular pattern (e.g., in rows), although a plurality of openings can be randomly placed as well. Further, a plurality of openings in a body can be configured so that any one opening extends the same or a different distance into the body relative to any other opening in the body.

In some forms, a persistent material body opening having a generally longitudinal axis can be configured so that this axis forms a particular angle with the plane defining a body surface from which the opening extends. For example, such a longitudinal opening axis can form an angle with a persistent material body surface that is approximately 90°. Alternatively, such an angle can be other than 90°, e.g., ranging from about 30° to about 89°, and in some instances, from about 45° to about 89°. Also, in some embodiments, persistent material body openings, whether extending partially or entirely through a persistent material body segment (e.g., a body wall), have a smaller cross sectional area at or near a persistent material body surface configured to be positioned at a bodily structure for anchoring to that bodily structure relative to its cross sectional area further away from this surface.

When a construct of the present invention utilizes a bioresorbable, or bioabsorbable material, a variety of such materials may be employed. Illustratively, suitable bioresorbable, or bioabsorbable polymers include but are not limited to poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyhydroxyalkanaates, polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, and polyphosphazenes. These or other bioresorbable materials may be used, for example, where only a temporary blocking or closure function is desired, and/or in combination with non-bioresorbable materials where only a temporary participation by the bioresorable material is desired.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A medical device for implantation in a bodily vessel of a patient to form a tubular graft anchored and supported in position by tissue of the patient, comprising:
    a) an implantable graft structure, the implantable graft structure comprised of a tubular body of persistent material having a first face on an exterior of the tubular body and configured for opposing a bodily vessel wall upon implantation, and a second face on an interior of the tubular body, wherein said persistent material comprises a first longitudinal region containing one or more openings extending from the first face to the second face, a second longitudinal region that does not contain openings extending from the first face to the second face, and a third longitudinal region containing one or more openings extending from the first face to the second face, wherein the second longitudinal region is positioned longitudinally between the first longitudinal region and the third longitudinal region;
    b) a tissue ingrowth material positioned against the second face on the interior of the tubular body and extending over the one or more openings in the first longitudinal region and the third longitudinal region and beyond edges of the one or more openings in the first longitudinal region and the third longitudinal region to cover regions of the second face around the one or more openings in the first longitudinal region and third longitudinal region, the tissue ingrowth material configured for receiving tissue ingrowth from the bodily vessel wall effective to anchor the graft structure to the bodily vessel wall with ingrown tissue of the patient; and
    c) a first bioabsorbable expandable frame element positioned within the first longitudinal region of the tubular body and a second bioabsorbable expandable frame element discrete from the first bioabsorbable expandable frame element and positioned within the third longitudinal region of the tubular body, the first bioabsorbable stent expandable frame element and the second expandable bioabsorbable frame element effective when expanded to hold the tubular body of persistent material in place in the bodily vessel for a duration sufficient for tissue ingrowth from the bodily vessel wall into the tissue ingrowth material so as to anchor the graft structure to the bodily vessel wall with ingrown tissue of the patient, the at least one first and second bioabsorbable frame elements thereafter being bioabsorbed to leave the tubular body of persistent material supported by the ingrown tissue of the patient.

2. The medical device of claim 1, wherein the tubular body of persistent material comprises a persistent synthetic polymeric material.

3. The medical device of claim 1, wherein the tissue ingrowth material comprises collagen.

4. The medical device of claim 3, wherein the tissue ingrowth material comprises an extracellular matrix material.

5. The medical device of claim 4, wherein the extracellular matrix material retains at least one growth factor native to a tissue source for the extracellular matrix material.

6. A method for treating a patient to form a tubular graft anchored and supported in position by tissue of the patient, the method comprising implanting in a bodily passage of the patient a medical device according to claim 1.

7. The medical device of claim 1 wherein said openings comprise slits or rectilinear or curvilinear voids.

8. A medical device for implantation in a bodily vessel of a patient to form a valved tubular graft anchored and supported in position by tissue of the patient, comprising:
   a) an implantable graft structure comprising a tubular body of persistent material having a first face on an exterior of the tubular body and configured for opposing a bodily vessel wall upon implantation, and a second face on an interior of the tubular body, wherein said persistent material comprises a first longitudinal region containing one or more openings extending from the first face to the second face, a second longitudinal region that does not contain openings extending from the first face to the second face, and a third longitudinal region containing one or more openings extending from the first face to the second face, wherein the second longitudinal region is positioned longitudinally between the first longitudinal region and the third longitudinal region;
   b) a tissue ingrowth material positioned against the second face on the interior of the tubular body and extending over the one or more openings contained in the first longitudinal region and the third longitudinal region and beyond edges of the one or more openings contained in the first longitudinal region and the third longitudinal region to cover regions of the second face around the one or more openings contained in the first longitudinal region and the third longitudinal region, the tissue ingrowth material configured for receiving tissue ingrowth from the vascular vessel wall effective to anchor the graft structure to the bodily vessel wall with ingrown tissue of the patient;
   c) a first bioabsorbable expandable frame element positioned within the first longitudinal region of the tubular body and a second bioabsorbable expandable frame element discrete from the first bioabsorbable expandable frame element and positioned within the third longitudinal region of the tubular body, the first bioabsorbable expandable frame element and the second expandable bioabsorbable expandable frame element effective when expanded to hold the tubular body of persistent material in place in the bodily vessel for a duration sufficient for tissue ingrowth from the bodily vessel wall into the tissue ingrowth material so as to anchor the graft structure to the bodily vessel wall with ingrown tissue of the patient, the first bioabsorbable expandable frame element and the second bioabsorbable expandable frame element thereafter being bioabsorbed to leave the tubular body of persistent material supported by the ingrown tissue of the patient; and
   d) a valve having one or more valve leaflets supported by the tubular body of persistent material and located within the tubular body longitudinally between the first bioabsorbable expandable frame element and the second bioabsorbable expandable frame element, the valve responsive to fluid flow within the bodily vessel.

9. The medical device of claim 8, wherein the first and second bioabsorbable expandable frame elements comprise a bioabsorbable polymer.

10. The medical device of claim 8, wherein the first bioabsorbable expandable frame element and the second bioabsorbable expandable frame element are self-expanding frame elements.

11. The medical device of claim 9, wherein the bioabsorbable polymer is poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyhydroxyalkanaates, polyphosphoester, polyphosphoester urethane, poly(amino acids), cyanoacrylates, poly(trimethylene carbonate), poly(iminocarbonate), copoly(ether-ester), polyalkylene oxalate, or polyphosphazene.

12. The medical device of claim 8, wherein the one or more openings defined in the tubular body of persistent material include at least one slit.

13. The medical device of claim 8, wherein the tubular body of persistent material is comprised of a naturally-derived biocompatible material.

14. The medical device of claim 8, wherein the tubular body of persistent material is comprised of a collagen-containing material.

15. The medical device of claim 8, wherein the tubular body of persistent material is comprised of a non-naturally derived biocompatible material.

16. The medical device of claim 8, wherein the tubular body of persistent material is comprised of a synthetic polymeric material.

17. The medical device of claim 16, wherein the tubular body of persistent material is comprised of polytetrafluroethylene.

18. The medical device of claim 16, wherein the synthetic polymeric material is comprised of polyurethane.

19. The medical device of claim 8, wherein the tubular body of persistent material comprises a sheet-form material.

20. The medical device of claim 8, wherein the tubular body of persistent material comprises a non-sheet-form material.

21. The medical device of claim 8, wherein the tubular body of persistent material comprises a hollow and generally cylindrical tube of material.

22. The medical device of claim 8, wherein the tissue ingrowth material is comprised of a naturally-derived biocompatible material.

23. The medical device of claim 8, wherein the tissue ingrowth material is comprised of a remodelable material.

24. The medical device of claim 8, wherein the tissue ingrowth material is comprised of a collagen-containing material.

25. The medical device of claim 8, wherein the tissue ingrowth material is comprised of an extracellular matrix material.

26. The medical device of claim 25, wherein the extracellular matrix material comprises serosa, pericardium, dura mater, peritoneum, or dermal collagen.

27. The medical device of claim 25, wherein the extracellular matrix material comprises submucosa.

28. The medical device of claim 27, wherein the submucosa comprises porcine submucosa.

29. The medical device of claim 27, wherein the submucosa comprises small intestine submucosa, urinary bladder submucosa, or stomach submucosa.

30. The medical device of claim 8, wherein the tissue ingrowth material is comprised of a first tubular piece of tissue ingrowth material covering the one or more openings contained in the first longitudinal region and a second tubular piece of tissue ingrowth material discrete from the first tubular piece of tissue ingrowth material and covering the one or more openings contained in the third longitudinal region.

31. The medical device of claim 8, wherein the tissue ingrowth material is comprised of a synthetic polymeric material.

32. A method for treating a patient to form a valved tubular graft anchored and supported in position by tissue of the patient, the method comprising implanting in a bodily vessel of the patient a medical device according to claim 8.

33. The medical device of claim 8 wherein said openings comprise slits or rectilinear or curvilinear voids.

* * * * *